United States Patent [19]
Remmereit

[11] Patent Number: 6,019,990
[45] Date of Patent: Feb. 1, 2000

[54] CONJUGATED LINOLEIC ACID DELIVERY SYSTEM IN COSMETIC PREPARATIONS

[75] Inventor: Jan Remmereit, Volda, Norway

[73] Assignee: Natural Nutrition Ltd. AS, Norway

[21] Appl. No.: 08/975,748

[22] Filed: Nov. 21, 1997

[51] Int. Cl.[7] ..................................................... A61K 7/00
[52] U.S. Cl. ....................... 424/401; 514/844; 514/937; 514/969; 424/59
[58] Field of Search ............... 424/401, 59; 514/844, 514/845, 846, 847, 937, 938, 969, 557

[56] References Cited

U.S. PATENT DOCUMENTS

| | | | |
|---|---|---|---|
| 4,393,043 | 7/1983 | Koulbanis et al. | 424/59 |
| 4,528,283 | 7/1985 | Lang et al. | 514/55 |
| 4,661,343 | 4/1987 | Zabotto et al. | 424/59 |
| 4,822,598 | 4/1989 | Lang et al. | 424/47 |
| 5,543,136 | 8/1996 | Aldous | 424/59 |
| 5,573,755 | 11/1996 | Franklin et al. | 424/59 |
| 5,574,063 | 11/1996 | Perricone | 514/474 |
| 5,607,664 | 3/1997 | Ascione et al. | 424/59 |
| 5,670,139 | 9/1997 | Allard et al. | 424/59 |
| 5,676,934 | 10/1997 | Siegfried | 424/59 |

*Primary Examiner*—Jose' G. Dees
*Assistant Examiner*—Michael A. Williamson
*Attorney, Agent, or Firm*—Medlen & Carroll, LLP

[57] ABSTRACT

New cosmetic formulations containing free and derivatized forms of conjugated linoleic acid. These ingredients have beneficial effects related to their medicinal and nutritional properties, but also are engineered for their compatibility with standard cosmetic ingredients. Certain vitamin/conjugated linoleic acid combinational molecules are described which deliver equimolar amounts of both free components to viable layers of the epidermis, thereby obtaining multiple functionality of the final product.

4 Claims, No Drawings

CONJUGATED LINOLEIC ACID DELIVERY SYSTEM IN COSMETIC PREPARATIONS

FIELD OF THE INVENTION

This invention relates to cosmetic preparations such as skin creams and balms, face cleansers, hand moisturizers, skin toners, and sunscreens. More particularly, it relates to a delivery system for the penetration and release into the lower levels of the skin of conjugated linoleic acid compounds, together with other optional fat soluble medicaments, for example vitamins A, D, and E to provide antiageing, moisture stabilization, and bioprotection functions.

BACKGROUND OF THE INVENTION

Even though cosmetic preparations have been a staple of commerce for centuries, there continues to be a continual expansion of cosmetic markets, and proliferation of new products. The field of skin care products has grown tremendously as new naturally occurring and synthetic polymeric materials have been identified. Processing equipment and techniques have also become more sophisticated, so that many of the current cosmetic products available over the counter, have a high level of uniformity and wholesomeness, but also impart substantive pharmacologic and nutritive properties not realized in older preparations.

The goal of modern cosmetics is to achieve multiple effects simultaneously, such as moisturizing, increased pliancy, drug or nutrient delivery, texturizing, environmental protection, and coloration. Some of these objectives inherently require substances which are water compatible such as humectants, and others require lipid compatible substances such as emollients. The largest class of cosmetic mixtures are emulsions of oil and water based fractions, and may be either oil in water (O/W) or water in oil (W/O), or both. For a review of the various physical forms and processes of making mixtures such as true emulsions, microemulsions, gels, and liposomes, see Fox, C., "Cosmetic Vehicles., Advances in Cosmetic Science and Technology, part 4," Cosmetics and Toiletries, 110: 59 (1995).

These emulsions have both occlusivity and humectancy. In occlusivity, a non-irritating moisture barrier is established on the surface of the skin, to prevent loss of moisture. Typical materials are petroleum jelly, mineral or vegetable oils, silicones, waxes, fatty acids, and esters. Typical humectants, which attract water and help bind water to the skin, include glycerin, sorbitol, sodium lactate, and sodium pyrollidone carboxylate, are beneficial in hydrating the stratum corneum and improving its viscoelastic behavior (See Williams and Schmitt, eds., Chemistry and Technology of the Cosmetics and Toiletries Industry, 2nd ed., Blackie Academic and Professional, London: 1996).

Most emulsions require one or more stabilizers to maintain the microdispersion, and to prevent collapse and separation of the blend. A widely used stabilizer system utilizes stearic acid in the oil phase, and tri-, di-, or monoethanolamine in the aqueous phase. The resulting ethanolamine stearate is an excellent stabilizer. Combinations of intermediate chain length (C6–C12) aliphatic alcohols, esters, and carboxylic acids may act as stabilizers. Cetyl alcohol (C16) is commonly used in conjunction with triethanolamine to impart both soft "feel" and stabilization of the emulsion. Cetyl palmitate, isolated from natural sources, is a preferred stabilizer and carrier for other ingredients.

Many cosmetic preparations require thickeners to provide the desired viscosity. These thickeners are often used when the lubricity of the oil fraction is heightened by a high unsaturated oil composition of the cosmetic. Typical thickeners include coconut diethanolamide, cellulose and certain ether derivatives such as hydroxyethylcellulose or hydroxypropylcellulose, carrageenan, which is a linear sulfated polysaccharide of D-galactose and D-anhydrogo-D-galactose. For a good discussion of the role of thickeners in cosmetic preparation, see Knowlton, et al., eds., Handbook of Cosmetic Science and Technology, 1st ed., Elsevier, Oxford: 1993).

Since the advent of polymer surfactant chemistry, a large and varied number of surface active compounds have been available for incorporation into cosmetics. Because surfactants tend to mobilize natural lipid, there is a pronounced tightening effect on the skin associated with their use, presumably by their residues binding to keratin. This effect is most severe using sodium lauryl sulfate, and is much diminished in the use of potassium myristate. The use of surfactants, of course, has an important cleaning function, so that they are common ingredients in cleansing creams. Since these creams are first spread onto the skin and then removed almost immediately by tissue wiping, surface contact is minimized.

There have been many studies of cosmetic additives which enhance the penetration of the beneficial ingredients into the lower strata of the epidermis. Similarly there have been many studies of the physiology, histology, and biochemistry of the epidermis and dermis and their relation to absorption. Among those compounds studied, the following have been identified as promoting adsorption and penetration (also termed "flux") of chemicals through the lipid-dominated interstices between cells of the lamellar layer: propylene glycol either alone or in combination with unsaturated fatty acids, and propylene glycol diesters of caprylic and capric acids. Solvents such as DMSO, ethanol, hihydrotetrafuran, and isopropanol are known to deplete interstitial lipids leading to increased penetration of indicator drugs. These may be useful for "patch" type drug delivery devices, but have limited value in routine cosmetics because of their irritant properties. The goal of these ingredients is to promote adsorption and migration of beneficial substances through the lipid deposits without disrupting the essential structure of the skin.

A popular class of cosmetic additives (15 percent of total cosmetic sales) is the so-called sunscreens. UV light from the sum has a spectrum of wavelengths ranging from 400 nm down to less than 290 nm. Light having a wavelength of 400–320 is known as UV-A, that having a wavelength of 320–290 is called UV-B, and that having a wavelength of less than 290 nm is UV-C. UV-B has the greatest potential for causing skin damage and is associated with accelerating skin ageing, wrinkling, epidermal cracking and scaling, and more serious conditions such as basal cell carcinoma and melanoma. UV-A is associated with melanin production resulting in tanning. The desired function of a sunscreen is to absorb out the harmful UV-B light while allowing the UV-light to effect tanning. Ideally a sunscreen will shield the skin from a portion of the UV-A light as well as the UV-B because overexposure to UV-A can also cause skin damage.

Conventional sunscreen compounds that absorb UV-B light include benzophenone-3, benzophenone -4, and benzophenone-8, 4-methoxycinnamic acid salts, parabenzoic acid, substituted parabenzoic acid and salts thereof, glyceryl parabenzoic acid, menthyl anthranilate, $TiO_2$ and ZnO. UV-A is effectively absorbed by butyl methoxydibenzoyl methane. While most sunscreen compounds are spread onto skin in liquid form, dry compositions have been disclosed in U.S. Pat. No. 5,676,934. Other sunscreen formulations of interest are the stabilized preparations disclosed in U.S. Pat. Nos. 5,670,139, 5,573,755 (hydroxy salts of metallic ions), U.S. Pat. No. 5,543,136 (conventional titanium and zinc oxides in a smooth, even flowing emulsion stabilized with tridecyl polymers). Finally, certain compounds have been shown to enhance the activity and effectiveness of conventional classes of sunscreen compounds, as disclosed in U.S. Pat. No. 5,607,664.

In the formulation of cosmetic preparations, most of the additive ingredients, e.g. humectants, sunscreens, surfactants, thickeners, etc. are present in low concentrations ranging from 0.1 to about 10 percent. Sunscreen concentrations are illustrative, and are also regulated by domestic and foreign governmental agencies, as set forth in the Cosmetic Handbook, supra: bendzophenone-3 (2–6%), benzophenone-4 (5–10%), benzophenone-8 (3%), 4-methoxycinnimic acid salts (8–10%), parabenzoic acid (1–5%), and butyl methoxydibenzoyl methane (5% maximum). The major difference in formulary is whether the emulsion is an O/W or a W/O. Obviously there will be a widely differing overall oil content in a W/O preparation. In the case of a high oil content all purpose cream, a typical will have sensory components (stearic acid, cetyl alcohol, microcrystalline wax, glyceryl monostearate and the like in a concentration of 0.5 to 3 percent, but the combination of mineral oil and petrolatum will approach 50 percent. In contrast, a hydroalcoholic astringent will contain nearly 50 percent ethyl alcohol, witch hazel extract, and glycerine. In a low oil formulation, the oil content may be only a few percent, and the texture of the preparation will rely upon thickeners and emulsion stabilizers such as triethanolamine in combination with stearic acid.

There have been many variations of cosmetic preparations incorporating skin active agents in delivery systems of varying efficiency. U.S. Pat. No. 5,618,850 discloses a preparation incorporating alpha-hydroxy acid salts such as lactate and glyconate. The alpha-hydroxyacids have attracted much attention for their ability to control skin texture and wrinkling, and to confer beneficial effects in treating mild skin conditions. U.S. Pat. No. 4,393,043 is interesting in that it discloses the enrichment of cosmetic preparations with essential fatty acids including linoleic acid and conjugated linoleic acids, but only at the levels found in jojoba oil. In a similar disclosure in U.S. Pat. No. 4,661,343 an essentially anhydrous preparation utilizes karite oil to impart a mixture of fatty acids including linoleic acid in a concentration of 2 to 5 percent.

SUMMARY OF THE INVENTION

One purpose of cosmetic preparations is to deliver beneficial substances to the active site within the epidermis or dermis so that they may act to improve skin appearance, function, and well-being. Frequently the molecular characteristics of the beneficial substance are incompatible with the environment that substance must traverse to arrive at the active site. It is therefore an object of the present invention, to provide cosmetic formulations whose ingredients facilitate the transport and delivery of active agents to the sites where they may exert their intended effects. Since the cellular interstices of the lamellar layer of the epidermis are filled with highly lipophilic substances, it has been found that relatively nonpolar molecules are more readily transported across this barrier to the lower layers of the epidermis, most desirably to the epidermal/dermal interface at which the basal cells actively form successive generations of keratocytes.

It is an object of the present invention to provide a mixture of cosmetic ingredients which promotes the transport of conjugated linoleic acids (CLA) across the epidermis to bring them to the viable cell layers. Uptake of CLA into cellular lipids is associated with anticarcinogenesis, lipid repartitioning, and other beneficial physiological effects. Since linoleic acid is an essential fatty acid, its conjugated forms are readily absorbed into lipids and fats. Theoretically conversion of ordinary linoleic acid to conjugated linoleic acid results in eight isomers. The isomers of greatest interest in the present cosmetic preparations are cis9,trans11-linoleic acid and trans10,cis12-linoleic acid, since these isomers are most commonly associated with physiological benefits, and are most easily made from natural sources such as seed oils. Hereinafter the term "19,11-linoleic" or "10,12-linoleic" shall mean preferentially these two main isomers, but will include lesser amounts of the remaining six isomers, particularly when obtained or derived from a natural source.

In accordance with the present invention, 9,11-linoleic acid and 10,12-linoleic acid are formulated into cosmetic preparations either as the free acid, as individual chemical derivatives, or as combinations of free acid and derivative. Having a functional carboxylic acid group facilitates derivatization of the conjugated linoleate. Reaction of linoleic acid with the corresponding linoleyol results in the various ester combinations. Linoleyol can also be combined in an ester with retinoic acid for delivery vitamin A in a vehicle conjugate highly compatible with the free conjugated fatty acid. Of particular interest is an ester of ascorbic acid and conjugated linoleic acid, whose ester bond is highly sensitive to nonspecific naturally occurring epidermal esterases, which release both the intact antioxidant ascorbic acid and conjugated linoleic acid into the skin simultaneously.

The present invention therefore provides cosmetic preparations containing a cosmetically effective amount of conjugated linoleic acid containing compounds which include either individually or in combination free 9,11-linoleic acid, free 10,12-linoleic acid, 9,11-linoleyl-9,11 linoleate ester, 9,11-linoleyl-10,12-linoleate ester, 10,12-linoleyl-10,12-linoleate ester, 10,12-linoleyl-9,11-linoleate ester, ascorbyl-linoleate ester, ascorbyl-10,12-linoleate, 9,11-linoleyl-retinoate, 10,12-linoleyl-retinoate, and combinations thereof in a pharmaceutically or cosmetically acceptable carrier. Such carriers are most typically emulsions of an aqueous phase containing a humectant such as sorbitol, glycerine, polyalkylene oxide, dibutylphthalate, and a naturally occurring ingredient of sweat, sodium 2-pyrrolidone-5-carboxylate, or combinations, and a non-aqueous lipid compatible phase containing emollients including stearyl alcohol, glycerol monostearate, cetyl alcohol, cetyl palmitate, lanolin, isobutyl palmitate, glycol stearate, and emulsion stabilizers such as triethanolamine in combination with stearic acid or other C-8 to C-26 saturated fatty acids, and chitosan deacetylated between 35 and 90 percent, or a mixture of chitosans deacetylated between 35 or lower and 90 percent or higher of its sugar residues.

One of the most prevalent human cancers is basal cell carcinoma of the skin. CLA and its derivatives for incorporation into proliferating skin cells as a prophylactic to reduce the incidence of carcinoma (or its more rare analog, melanoma), may be combined with incorporation of sun screen into cosmetic preparations to help reduce the total dose and penetration of carcinogenic UV-A and UV-B radiation and is a particularly efficacious aspect of the present cosmetic preparations. Typical UV light absorbing organic or inorganic compounds include homomenthol salicylate, 3-, 4-, or 6-benzophenone, 4-methoxycinnamic acid and its salts, parabenzoic acid and its derivatives such as glyceryl parabenzoic acid, menthyl anthranilate, butyl methoxydibenzoyl methane, titanium dioxide and zinc oxide. Combining the foregoing formulation with the linoleyl-ascorbate conjugate, further decreases carcinogenicity by providing a free radical scavenger upon hydrolysis of the ascorbate ester bond.

In a further aspect of the present invention, CLA is esterified to a long chain fatty alcohol of C6 to C22 straight chain or branched methylene groups. Upon cleavage by native esterase, the CLA is available for uptake, and the released fatty alcohol is metabolized or remains in the lipid occupied cellular interstices as a softener until sloughed by normal corneum replacement. The objective of incorporating such compounds into the present preparations is to reduce the polarity of the CLA, making it more compatible with the principal skin penetrants. This embodiment of the inventive preparations further contemplates mixtures of compounds of varying saturated fatty chain length, and also esters of CLA with polyols or ethoxyols of C4 to C14. The latter compounds are useful for their combination nonpolar water soluble and fat soluble moieties, which bridge the emulsion phases to provide emulsion stability.

While the carriers of the present invention are most preferably emulsions, and take the form of creams and lotions, pure lipophilic preparations suitable for lipstick and coating moisture barriers which are not readily displaced by water, especially in pharmaceutical preparations, are also contemplated. In such preparations the aqueous components are omitted. Such products containing medicaments such as antibiotics as well as CLA and its derivatives, are efficacious for wound healing and may be incorporated into an ointment base.

DETAILED DESCRIPTION OF THE PREFERRED EMBODIMENT

While fatty acids are known to promote transport of cosmetic preparations into the epidermis, nonpolar lipophilic compounds are nevertheless more compatible with the lipid constituents of the skin. Consequently, it is a strategy of the present invention to utilize carriers as transport vehicles to facilitate deposition of CLA and other bioactive substances at the target sites. One aspect of this strategy is to blend CLA with highly hydrophobic derivatives of CLA. The alkylene portion of the molecule will be highly miscible with the hydrophobic carrier. Thus, mixtures of conjugated linoleic acid and the linoleyl-linoleate esters have particular efficacy. An additional benefit is the action of nonspecific esterases in the tissues releases CLA from the ester carrier. By adjusting the pH and salt content of the preparation, the action of the esterases can be controlled to give a time delay effect, so that new CLA is constantly being made available between cosmetic applications.

It is essential for the practice of the invention to compound the cosmetic preparations from purified or partially purified CLA, rather than use an unfractionated seed oil source. While safflower, sunflower, and corn oil are important dietary sources of CLA, it is desirable to provide an enriched source in a cosmetic. Native refined seed oils have a relatively high proportion of other unsaturated fatty acids. Gamma-linoleic acid, in particular, and oleic and linolenic acids to a lesser extent, will be expected to compete metabolically with CLA for incorporation into cellular lipids. In general, CLA prepared by high temperature alkaline refining is an acceptable source of CLA even though it will contain a mixture of the eight possible isomers of conjugated linoleic acid. It is believed that the cis9,trans11-linoleic acid, and to some lesser extent trans10,cis12-linoleic acid, possess most of the biological activity, but this has not yet been proven conclusively. Once the biologically active isomers have been conclusively identified, and it is possible to preferentially synthesize or isolate those isomers independently of the less active or inactive forms, a corresponding adjustment in percentage composition can readily be made. In the cosmetic formulations, reference will be made to CLA, with the expectation that this term encompasses at least a threshold level of one or more of the active isomers without regard to the presence of isomers of lesser or no activity.

The esters of the present invention are synthesized according to standard chemistries. Typically the CLA acid and saturated or unsaturated alcohols are mixed in an excess of a solvent diluent in a reflux reactor fitted with a condenser. Dry heat is applied to the reactor to institute a reflux action. The reaction is continued for up to several hours until all the water of esterification is condensed off. Alternatively, esterification may be carried out with a catalyst and/or an immobilized lipase. Catalytic esterification is carried out under stirring and vacuum at 150°–180° C. for 1–5 hours. If lipase is used, the reaction temperature is 40°–60° C. The reaction is complete when no more water can be removed by a vacuum of 2 molar. Solvent is removed by rotary evaporation. The linoleyl-linoleate compounds appear as heavy oils with virtually no solubility in water. The semi-saturated esters are wax-like, particularly those formed from the higher molecular weight saturated alcohols. Those having good compounding properties include conjugated linoleyl-stearate ester, linoleyl-palmitate ester, and linoleyl-myristate ester. A very satisfactory carrier for free CLA is a linoleyl-stearate softened with linoleyl-linoleate emulsion stabilized with a polymer such as polyvinyl alcohol as primary stabilizer, and a nonionic surfactant as a secondary stabilizer. A number of contemporary emulsion systems are described in Knowlton and Pearce, *Handbook of Cosmetic Science and Technology* supra, p. 95. This mixture forms a good base carrier delivery system and provides a highly enriched source of CLA both temporally, and as a time release preparation. The lipophilic phase is finished out by addition of any of the following: cetyl alcohol, stearic acid, steareth-2, steareth-21, laureth-7 and PEG-stearate. An aqueous compatible humectant phase may be glycerine wetted with enough water to form the emulsion.

The CLA containing cosmetic preparations may incorporate other active ingredients which perform either a different or a complementary function. Ingredients of different function, e.g. antibiotics, anti-inflammatories, astringents, disinfectants, etc. may be of any type where no chemical or physiological incompatibility occurs. In some instances the formula may need to be altered to ensure the activity of the ingredient. For example, one of the organic iodine sanitizer compounds is active only at a pH above 8. Clearly the formulation cannot, in this instance, be compounded with chitosan in the aqueous phase, because of its insolubility at neutral or basic pH.

A greater challenge is to create multifunction product cosmetics where the combined functions are complementary. Since the incorporation of CLA reduces the incidence of carcinogen-induced skin carcinoma, and UV light enhances carcinoma incidence, combination of transportable CLA as a chemoprotectant with sunscreen agents and anti-oxidants provides a multifunctional product with beneficial attributes. For the effect of CLA on carcinogen induced carcinogenesis, see Clement, et al., CANCER Supplement, 74: 1050 (1994) and Belury, *Nutrition and Cancer*, p. 148 London: 1996). Other benefits of CLA are disclosed in U.S. Pat. No. 5,585,400 (attenuating allergic responses), U.S. Pat. No. 5,554,646 (reducing body fat), and U.S. Pat. No. 5,428,072 (increasing feed conversion in animals).

Compounding CLA in cosmetics with sunscreen agents may involve both organic and inorganic chemicals which trap or neutralize photons of harmful wavelength. Some emulsion formulas adaptable to the present cosmetic preparations are disclosed in U.S. Pat. Nos. 5,543,136, 5,573,755, and 5,607,664. In some instances, more than one sunscreen chemical can be incorporated simultaneously, to achieve synergistic results, as taught in U.S. Pat. No. 5,658,555. Antioxidant preparations have been disclosed in U.S. Pat. No. 5,652,263 incorporating retinoid compounds.

U.S. Pat. No. 5,574,063 discloses the use of ascorbate fatty acid esters in the treatment of psoriasis and other skin maladies. In one aspect of the present invention, a CLA ascorbate ester is included in the cosmetic preparation in combination with a sunscreen. Upon cleavage, the ascorbic acid acts as a free radical scavenger, and the CLA is incorporated into nascent keratocytes. A suitable carrier incorporates linoleyl-linoleate to ensure compatibility of the ingredients in an oil based cosmetic not containing waxes or waxy derivatives of saturated long chain fatty acids.

A suitable mono-substituted linoleyl ascorbate is synthesized from 5,6-benzylidene-L-ascorbic acid prepared by conventional methods. An N-oxysuccinimidyl ester of conjugated linoleic or retinoic acid may be prepared by reaction of di-N-oxysuccinimidyl carbonate (DSC) with conjugated linoleic or retinoic acid respectively, in chloroform in the presence of triethlamine. 5,6-benzylidene-L-ascorbic acid is allowed to react with N-oxysuccinimidyl linoleate or retinoate in N,N-dimethylformamide in the presence of a catalytic base such as pyridine or triethylamine. If a molar ratio of activated linoleate ester to ascorbic acid is from 1.1 to 1.5 is used, the product consists mainly of the 2-O-linoleate ester. The final product may be isolated on silica gel. Fractions containing the desired product are combined and concentrated under vacuum. The product is dissolved in minimal volume of methanol, palladium on carbon is added in a catalytic amount, and the slurry is hydrogenated to remove the benzylidene protective group. The methanol is removed under vacuum, and the final product may be purified on silica gel.

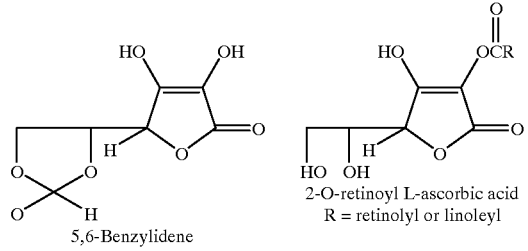

5,6-Benzylidene

2-O-retinoyl L-ascorbic acid
R = retinolyl or linoleyl

This protocol can be used to create the ascorbyl-retinoate molecule as well, which is useful in positioning both retinoic and ascorbic acids in a molar 1:1 ratio at the same skin loci. The ascorbyl-retinoate ester is fat soluble and CLA ester carriers are particularly effective as delivery systems to the epidermis.

Carriers are also of great benefit that not only act as efficient delivery vehicles for the active ingredients to the viable regions of the epidermis/dermis, but also those that promote uniform spreading of the product onto the skin surface. Compounds that promote film forming are especially useful in this application. One of the newer film forming compounds currently under investigation in cosmetics is chitosan, a form of deacetylated natural chitin. Once the acetyl group is removed to expose the amino group, the primary amine can be derivatized in a great variety of ways. U.S. Pat. Nos. 3,879,376 and 4,528,283 disclose several chitosan derivatives and their use in cosmetics. U.S. Pat. No. 4,822,598 discloses a class of quaternary derivatives of chitosan useful in cosmetic preparations.

In the cosmetic preparations of the present invention, it is desirable to utilize chitosan representing a spectrum of deacetylation ranging from 35 to 90 percent, and mixtures of chitosans of varying deacetylation. The choice of the combination depends on the degree of hydophobicity desired in the final mix. Under conventional conditions of controlled deacetylation, chitosan may be prepared containing both hydrophilic and hydrophobic domains capable of molecularly linking the lipid soluble CLA containing fraction and the humectant hydrophilic fraction in a single flowable film. This helps to stabilize the emulsion, to prevent phase separation and uneven spreading.

The term "cosmetically effective amount" means that amount of CLA or CLA ester or other derivative which achieves a desirable effect such as a chemiprotective effect or aids in making the skin more supple, pliant, and facilitates restoring or retaining moisture. Since the amount of any ingredient required to achieve such an effect will vary from one formulation to another depending on the other ingredients present, a cosmetically effective amount will frequently need to be established empirically. The following formulations are intended, without limitation, to provide some guide to formulating the classes of cosmetics set forth. Ingredients are sometimes expressed as ranges of percent. Reduction or increase in the presence of one ingredient, will necessarily correspondingly reduce or increase the proportion of one or more of the other ingredients.

| Illustrative Formula I. Skin cleaner and hand lotion. | |
|---|---|
| Part A. Oleophilic | |
| lanolin | 2.0–3.5 |
| stearic acid | 4.0–6.0 |
| petrolatum | 10.0–15.0 |
| (conjugated) linoleyl-(conjugated) linoleate ester | 2.0–5.0 |
| CLA (60%) | 4.0–9.0 |
| water | Balance |
| Part B. Hydrophilic | |
| glycerin | 4.0–7.0 |
| triethanolamine | 0.5–2.0 |
| water | Balance |
| | 100.0% |

The oleophilic and hydrophilic fractions are separately mixed, and then combined in a standard emulsification procedure, as described in "Emulsifiers", in *The Handbook of Cosmetic Science and Technology*, supra.

| Illustrative Formula II. Sunscreen Lotion | |
|---|---|
| Capric/caprylic triglyceride | 12.0 |
| Mineral oil | 66.0 |
| PEG dilaurate | 6.0 |
| CLA (70%) | 11.0 |

Illustrative Formula II.
Sunscreen Lotion

| | |
|---|---|
| Linoleyl-linoleate ester | 3.0 |
| retinoyl-ascorbate ester | 1.0 |
| stearyl parabenzoic acid | 0.5 |
| titanium dioxide | 0.5 |
| | 100.0% |

Illustrative Formula III.
Heavy lotion.

| | |
|---|---|
| Part A. Oleophilic | |
| Stearic acid | 4.0–6.0 |
| linoleyl-stearate ester | 2.0–5.0 |
| linoleyl-linoleate ester | 2.0–5.0 |
| CLA (70%) | 6.0–8.0 |
| Cetyl alcohol | 1.0–3.0 |
| Glyercyl monostearate | 0.5–1.5 |
| Ascorbyl-linoleate ester | 3.0–4.0 |
| Lanolin | 7.0–10.0 |
| Part B. Hydrophilic | |
| Glycerin | 3.0–5.0 |
| Xanthum gum | 0.5–1.0 |
| Triethanolamine | 1.5–3.0 |
| Water | Balance |
| | 100.0% |

Illustrative Formula IV.
All purpose cream.

| | |
|---|---|
| Part A. Oleophilic fraction. | |
| Glyceryl monohydroxystearate | 2.0 |
| CLA (70%) | 6.5 |
| linoleyl-linoleate ester | 3.0 |
| Mineral oil | 10.0 |
| Cetyl octanoate | 8.0 |
| Ascorbyl-retinoate ester | 1.0 |
| Part B. | |
| Glycerin | 3.0 |
| Triethanolamine | 2.0 |
| Carbomer 941 surfactant | 6.0 |
| Chitosan 58–65% Deacetylated | 2.5 |
| Water (pH adjusted to 5.5) | 59.0 |
| | 100.0% |

What is claimed is:

1. A cosmetic preparation comprising a cosmetically effective amount of a conjugated linoleic acid containing a compound selected from the group consisting of free 9,11-linoleic acid, free 10,12-linoleic acid, and combinations thereof; and a cosmetically effective amount of an ester of conjugated linoleic acid selected from the group consisting of 9,11-linoleyl-9,11-linoleate ester, 9,11-linoleyl-10,12-linoleate ester, 10,12-linoleyl, 10,12-linoleate ester, 10,12-linoleyl, 9,11-linoleate ester, ascorbyl-9,11-linoleyl ester, ascorbyl-10,12-linoleate ester, ascorbyl-retinoate ester, linoleyl monoacylglycerate, and combinations thereof, the conjugated linoleic acid and the conjugated linoleic acid ester in a pharmaceutically or cosmetically acceptable carrier.

2. A cosmetic preparation for reducing sun induced carcinogenesis comprising a cosmetically effective amount of a conjugated linoleic acid containing compound selected from the group consisting of 9,11-linoleyl-9,11-linoleate ester, 9,11-linoleyl-10,12-linoleate ester, 10,12-linoleyl, 10,12-linoleate ester, 10,12-linoleyl-9,11-dilinoleate ester, ascorbyl-9,11-linoleate ester, ascorbyl-10,12-linoleate ester, ascorbyl-retinoate ester and combinations thereof, a UV light absorbing organic or inorganic compound, and a pharmaceutically or cosmetically acceptable carrier.

3. The cosmetic preparation of claim 2 wherein said UV absorbing organic or inorganic compound is selected from the group consisting of homomenthol salicylate, 3-benzophenone, 4-benzophenone, 8-benzophenone, 4-methoxycinnamic acid and salts thereof, parabenzoic acid, substituted parabenzoic acid and salts thereof, glyceryl parabenzoic acid, menthyl anthranilate, butyl methoxydibenzoyl methane, $TiO_2$, and ZnO.

4. A cosmetic preparation comprising a cosmetically effective amount of a conjugated linoleic acid containing compound selected from the group consisting of 9,11-linoleyl-9,11-linoleate ester, 9,11-linoleyl-10,12-linoleate ester, 10,12-linoleyl, 10,12-linoleate ester, 10,12-linoleyl, 9,11-linoleate ester, ascorbyl-9,11-linoleyl ester, ascorbyl-10,12-linoleate ester, ascorbyl-retinoate ester, linoleyl monoacylglycerate, and combinations thereof, in a pharmaceutically or cosmetically acceptable carrier.

* * * * *